United States Patent [19]

Parker

[11] Patent Number: 4,524,271

[45] Date of Patent: Jun. 18, 1985

[54] LASER BLOCKING SHUTTER

[75] Inventor: Donald W. Parker, Arcadia, Calif.

[73] Assignee: Cilco, Inc., Huntington, W. Va.

[21] Appl. No.: 487,117

[22] Filed: Apr. 21, 1983

[51] Int. Cl.$^3$ .............................................. G01D 5/36
[52] U.S. Cl. .................................... 250/233; 350/275
[58] Field of Search ................. 219/121 LA, 121 LB;
128/303.1, 395–398; 350/272, 273, 274, 275,
269; 250/232, 233, 351, 353, 237 R; 372/14, 13

[56] References Cited

U.S. PATENT DOCUMENTS

| | | | |
|---|---|---|---|
| 3,750,049 | 7/1973 | Dowley et al. | 372/14 |
| 3,942,878 | 3/1976 | Engel et al. | 219/121 LA |
| 4,004,146 | 1/1977 | Blunck | 250/233 |

*Primary Examiner*—David C. Nelms
*Attorney, Agent, or Firm*—Lyon & Lyon

[57] ABSTRACT

There is disclosed herein a shutter particularly useful in blocking laser energy, such as for an Nd:YAG laser used for laser surgery. The shutter includes a metal plate which is rotatable about an axis, and the metal plate has a series of substantially evenly spaced holes therethrough. A plastic ring is disposed on one surface of the plate and has a like series of holes. The holes allow radiation to pass through the plate and ring, and the sections of the plate and ring intermediate the holes block such radiation. The plate/ring is mounted within a housing and a shaft so that this assembly can be manually or automatically rotated. The housing includes a hole therethrough with which any one of the holes in the plate/ring may be aligned to allow the laser beam to pass. The shutter assembly may have a switch or other suitable sensor for sensing the position of the plate to indicate and insure that a hole (or a section between holes) of the plate and plastic ring is aligned with the hole in the housing.

7 Claims, 3 Drawing Figures

U.S. Patent  Jun. 18, 1985  4,524,271
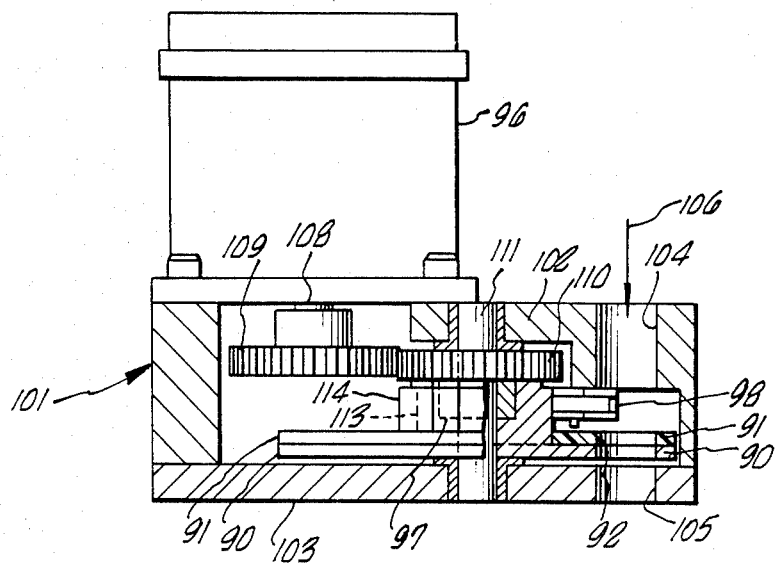
FIG. 1A
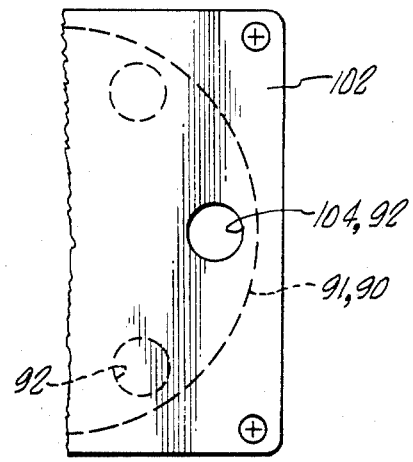
FIG. B
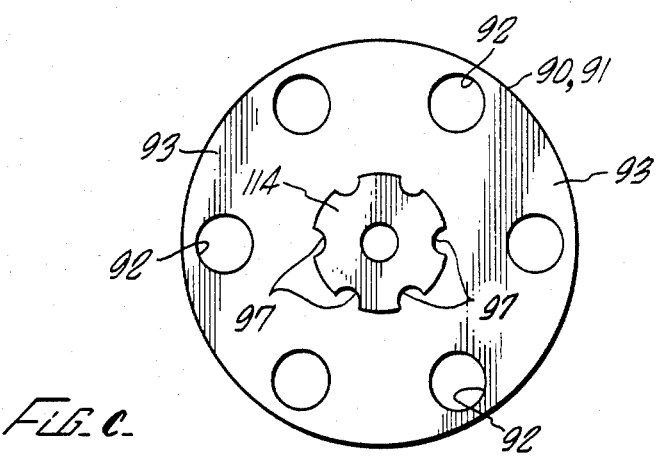
FIG. C

LASER BLOCKING SHUTTER

CROSS-REFERENCE TO RELATED APPLICATION

Reference is made to copending application, Ser. No. 487,118, filed Apr. 21, 1983 in the name of Bruce A. Burr, the disclosure of which is incorporated herein by reference.

BACKGROUND

The present invention relates to shutters, and more particularly to shutters useful for blocking laser energy.

Various forms of shutters have been developed for blocking and passing laser beams and laser pulses. Typically they comprise an iris form of device which can be opened and closed to pass or block the energy, or a flag type device which is used to selectively block the laser beam. Shutters of this nature which are designed for automatic operation generally use some form of push-pull solenoid system for opening and closing the iris or moving the shutter. Systems of this nature require power to maintain the shutter in a given position, and result in energy consumption and heat build up. For example, with the flag type shutter the solenoid is energized to turn "on" the system to move the flag to a position to pass the beam. Because of the consumption of current and heat build up such devices are of low reliability. Furthermore, when the shutter is closed, in the case of either the iris type or the flag type of shutter, the beam hits or impinges on the same point or area of the shutter and therefore the blocked beam can rapidly deteriorate the shutter.

SUMMARY

The shutter of the present invention comprises a rotatable plate with a plastic ring on the surface of the plate which receives the laser beam. The plate and ring have a series of substantially equally spaced holes therethrough through which the laser radiant energy may pass. The plate is arranged in a housing with an opening therethrough, which opening is aligned with the laser beam path. The plate is rotatable about the axis thereof so that the plate and ring can be moved to align any one of the holes therein with the hole through the housing to thereby pass the laser energy. Typically, the holes through the plate and ring are at sixty degree intervals. A solenoid stepping motor may be used to rotate the plate and ring in thirty degree increments such that the shutter is moved to an open position, then to a closed position, then to an open position, and so on. The plate preferably is formed of aluminum, and the ring preferably is formed of a plastic material, such as Delrin plastic. The shutter assembly may include a switch or other sensing means for detecting the position of the shutter so that an electrical signal can be provided to indicate whether the shutter is opened or closed.

Accordingly, it is a principal object the present invention to provide an improved form of shutter, particularly for use with lasers and the like.

Another object of this invention is to provide a rotatable shutter for use with lasers and the like, and wherein the shutter includes a plate with a plurality of openings therein such that the plate can be rotated from opened to closed positions to thereby pass and block a laser beam.

A further object of this invention is to provide a relatively inexpensive and reliable shutter for a laser beam.

These and other objects and features of the present invention will become better understood through a consideration of the following description taken in conjunction with the drawing in which:

FIG. 1a is a cross-sectional view of an exemplary shutter according to the present invention;

FIG. 1b is a partial front view of the shutter of FIG. 1a; and

FIG. 1c shows the shutter plate and ring used in the shutter.

DETAILED DESCRIPTION

The purpose of a shutter according to the present invention is to completely block or pass a laser beam. An example is a treatment beam from a laser such as an Nd:YAG laser, an aiming beam from a laser such as a He:Ne laser, or a combined beam from both such lasers. A laser surgery system using such laser beams, and using shutters according to the present invention is more fully described in said copending application. The shutter shown in the drawing need only be energized when it is necessary to shift from one position to another (from open to closed or from closed to open) and thus does not require power when it is in one of these two positions. A different part of the shutter is used for each successive "off", or closed, position to minimize damage and deterioration of the shutter.

The primary component in an exemplary embodiment of the shutter is a circular aluminum plate 90 and ring of black Delrin plastic 91. Both have a series of spaced circular holes or apertures 92 through which the laser beam may pass, and solid areas 93 between each such aperture. The plate assembly 90-91 is rotated by a stepping motor 96 in thirty degree increments. Recesses or other suitable depressions 97 are provided in the side of a hub 114 to allow a microswitch 98 to sense the position of the plate assembly 90-91 and to provide an electrical signal which indicates, and therefore confirms, that the shutter is in the proper open or closed position.

Considering the shutter assembly in greater detail, the stepping motor 96 may be a Ledex stepping solenoid, and the same is attached to a housing 101 having a front cover 102 and a back cover 103 with respective apertures 104 and 105 through which the laser beam passes as indicated by an arrow 106 when the shutter is open (holes 92 lined up with apertures 104–105). The shaft 108 of the solenoid 96 is connected to a first gear 109 which in turn is meshed with a second gear 110 disposed on a shaft 111. The shaft 111 is disposed in suitable bushings in the housing 101. The purpose of the gears 109 and 110 is to transmit the motion from the shaft 108 of the solenoid 96 to the plate assembly 90-91 and to reduce the size of the shutter package. It will be seen from FIG. 1a that the gear 110 is keyed by a pin 113 to a hub 114 of the plate 90. This arrangement causes the plate 90 and ring 91 to be rotated by the stepping solenoid 96.

The plate 90 for an exemplary shutter may be approximately three inches in diameter and approximately one-sixteenth inch thick. The holes 92 may be one-half inch disposed sixty degrees apart. The Delrin ring 91 preferably is approximately one-eight inch thick, and is secured to the plate in any suitable manner such as by several screws or the like. The Delrin ring transmitts IR, but it is opaque to visible radiation. The laser beam strikes the Delrin ring 91 when the shutter is closed, and the mechanical energy of the beam is absorbed by the ring 91 and the IR energy is stopped by the aluminum plate 90. If only an aluminum plate 90 were used, it would electrically conduct due to the intense IR energy and eventually deteriorate or break down.

The microswitch 98 is suitably mounted within the housing 101 and arranged to detect the open (or closed if desired) position of the shutter by detecting the detents or depressions 97. Any other suitable microswitch or proximity sensor can be used to determine when the shutter is open to the laser beam.

It thus will be understood that the stepping solenoid 96 can receive suitable electric signals and cause the plate assembly 90-91 to step in thirty degree increments to open or close the shutter, and an indication of whether the shutter is closed or opened is provided by a signal from the microswitch.

While a presently preferred embodiment of the present invention has been illustrated and described, modifications and variations thereof will be apparent to those skilled in the art given the teachings herein, and it is intended that all such modifications and variations be encompassed within the scope of the appended claims.

What is claimed is:

1. A shutter for blocking a laser beam comprising
   a metal plate,
   a plastic ring adjacent the plate, the plate and ring having a plurality of substantially equally spaced holes and solid areas between the holes, the holes providing a path for passing a laser beam,
   housing means for housing the plate and ring and for allowing the plate and ring to be rotated in a stepwise fashion, said housing means being adapted to support the plate and ring to allow a laser beam to pass through a hole in the plate and ring assembly, and
   means for rotating said plate and ring assembly.

2. A shutter for blocking a laser beam comprising
   a metal plate and plastic ring adjacent the plate, the plate and ring having a plurality of substantially equally spaced holes and solid areas between the holes, the holes providing a path for passing a laser beam,
   housing means for housing the plate and ring and for allowing the plate and ring to be rotated in a stepwise fashion, said housing means having an opening therethrough for allowing a laser beam to pass through the opening and to pass through a hole in the plate and ring assembly when a hole thereof is aligned with the opening in said housing, and
   means for rotating said plate and ring assembly.

3. A shutter in claim 2 including
   detector means for detecting the position of holes in the plate and ring assembly with respect to the opening in the housing and for providing an electrical signal indicative of the open or closed position of the shutter.

4. A shutter as in claim 2 wherein
   said holes in said plate and ring are disposed at substantially sixty degree intervals, and
   said means for rotating said plate and ring assembly comprises stepper motor means for advancing said plate and ring in thirty degree steps.

5. A shutter for blocking a laser beam comprising
   a metal plate and plastic ring adjacent the plate, the plate and ring having a plurality of substantially equally spaced holes and solid areas between the holes, the holes providing a path for passing a laser beam, said holes in said plate and ring being disposed at substantially sixty degree intervals, and
   housing means for housing the plate and ring and for allowing the plate and ring to be rotated in a stepwise fashion, said housing means having an opening for allowing a laser beam to pass through the opening and to pass through a hole in the plate and ring assembly when a hole thereof is aligned with the opening in said housing, and
   stepper motor means for rotating said plate and ring assembly in substantially thirty degree steps.

6. A shutter as in claim 5 including
   detector means for detecting the position of holes in the plate and ring assembly with respect to the opening in the housing and for providing an electrical signal indicative of the open or closed position of the shutter.

7. A shutter for blocking a laser beam comprising
   an aluminum plate and plastic ring secured to a face of the plate, the plate and ring having a plurality of aligned holes spaced at approximately sixty degree intervals and having solid areas between the holes, the holes providing a path for passing a laser beam,
   housing means for housing the plate and ring and for allowing the plate and ring to be rotated in a stepwise fashion, said housing means having an opening therethrough for allowing a laser beam to pass through the opening and to pass through a hole in the plate and ring assembly when a hole thereof is aligned with the opening in said housing,
   stepper means for rotating said plate and ring assembly in substantially thirty degree steps, and
   detector means for detecting the position of holes in the plate and ring assembly with respect to the opening in the housing and for providing an electrical signal indicative of such position.

* * * * *